United States Patent [19]

Livingston

[11] Patent Number: 5,320,111
[45] Date of Patent: Jun. 14, 1994

[54] LIGHT BEAM LOCATOR AND GUIDE FOR A BIOPSY NEEDLE

[75] Inventor: Troy W. Livingston, Northbrook, Ill.

[73] Assignee: Livingston Products, Inc., Wheeling, Ill.

[21] Appl. No.: 944,474

[22] Filed: Sep. 14, 1992

Related U.S. Application Data

[63] Continuation-in-part of Ser. No. 831,215, Feb. 7, 1992.

[51] Int. Cl.⁵ ............................................. A61B 10/00
[52] U.S. Cl. ................................. 128/754; 128/665; 128/653.1; 606/130; 378/37; 378/206
[58] Field of Search ............... 128/754, 753, 752, 751, 128/749, 664, 665, 653.1, 662.05, 663.01; 606/130; 604/116; 378/37, 204, 205, 206; 359/618, 629

[56] References Cited

U.S. PATENT DOCUMENTS

| | | | |
|---|---|---|---|
| 4,296,329 | 10/1981 | Mirabella | 250/491 |
| 4,385,397 | 5/1983 | Verro | 378/20 |
| 4,563,768 | 1/1986 | Read et al. | 378/37 |
| 4,651,732 | 3/1987 | Frederick | 606/130 |
| 4,750,487 | 6/1988 | Zanetti | 606/130 |
| 4,836,671 | 6/1989 | Bautista | 356/1 |
| 4,930,143 | 5/1990 | Lundgren et al. | 378/37 |
| 5,031,203 | 7/1991 | Trecha | 378/205 |
| 5,040,872 | 8/1991 | Steinle | 359/638 |
| 5,053,042 | 10/1991 | Bidwell | 606/130 |
| 5,078,142 | 1/1992 | Siczek et al. | 128/653.1 |
| 5,107,843 | 4/1992 | Aarnio et al. | 128/662.05 |
| 5,155,623 | 10/1992 | Miller et al. | 359/495 |

Primary Examiner—Stephen C. Pellegrino
Assistant Examiner—Guy V. Tucker
Attorney, Agent, or Firm—Fitch, Even, Tabin & Flannery

[57] ABSTRACT

Method and apparatus for locating and guiding a biopsy needle with respect to an X-rayed specimen having a tumor to be engaged by the needle. Intersecting laser beams are utilized to mark the location of the tumor and to guide the biopsy needle in a vertical path. The laser beam source is movable in orthogonal paths while compensating means redirect the beams to maintain them within a target area or eliminate any parallax. That is, the angular position of the laser light beam is adjusted to different angles at different coordinate positions to have the needle follow along a portion of a straight line path from the X-ray point source through the lesion and to the X-ray film. Thus, the needle tip should not be displaced to one side of a small lesion.

9 Claims, 11 Drawing Sheets

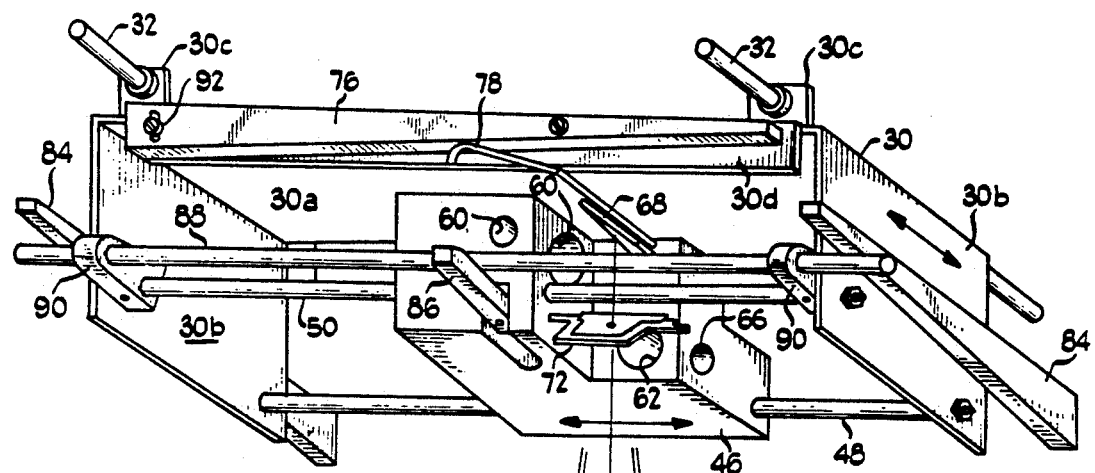
_Fig 3_
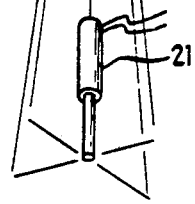
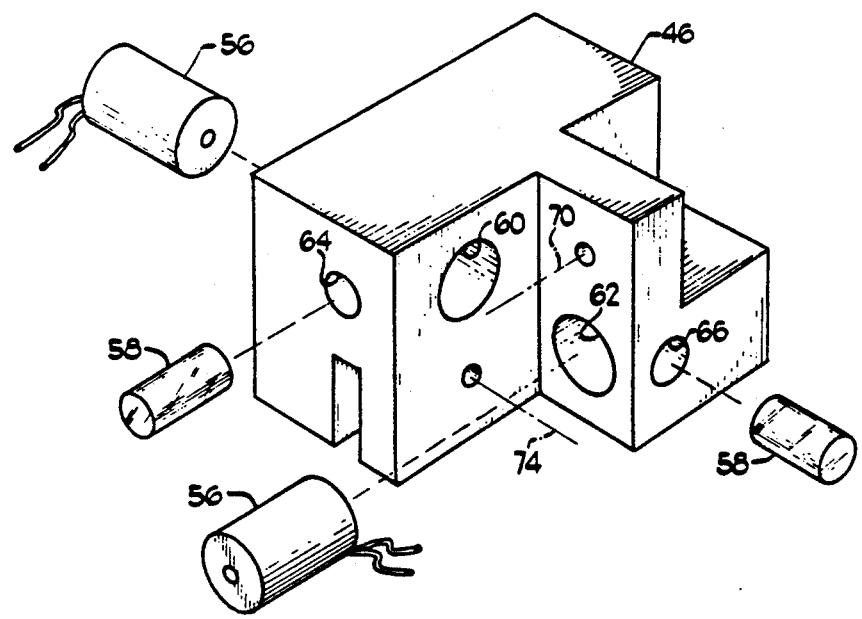
_Fig 4_

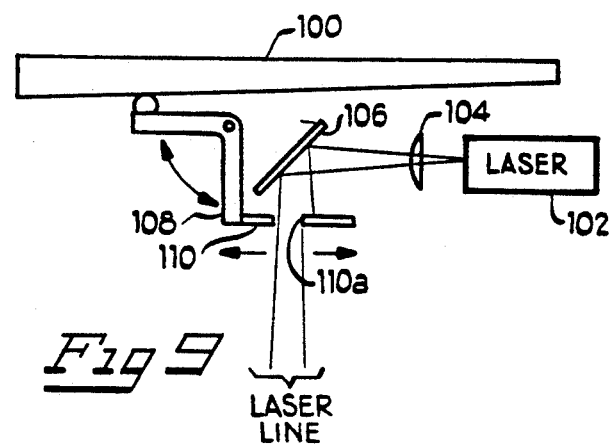
*Fig 9*
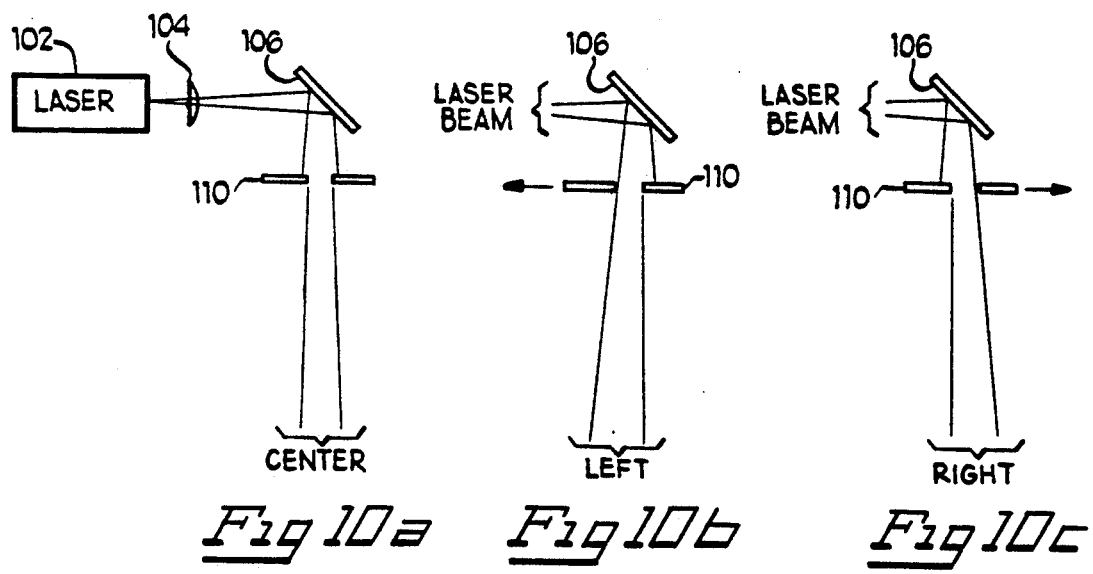
*Fig 10a*   *Fig 10b*   *Fig 10c*

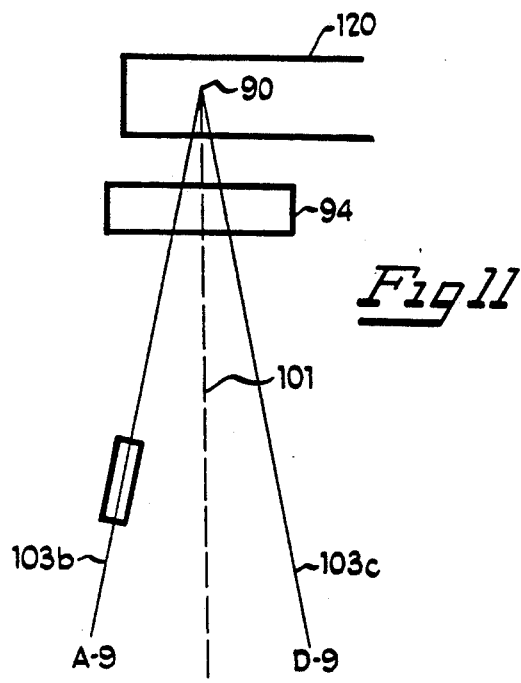
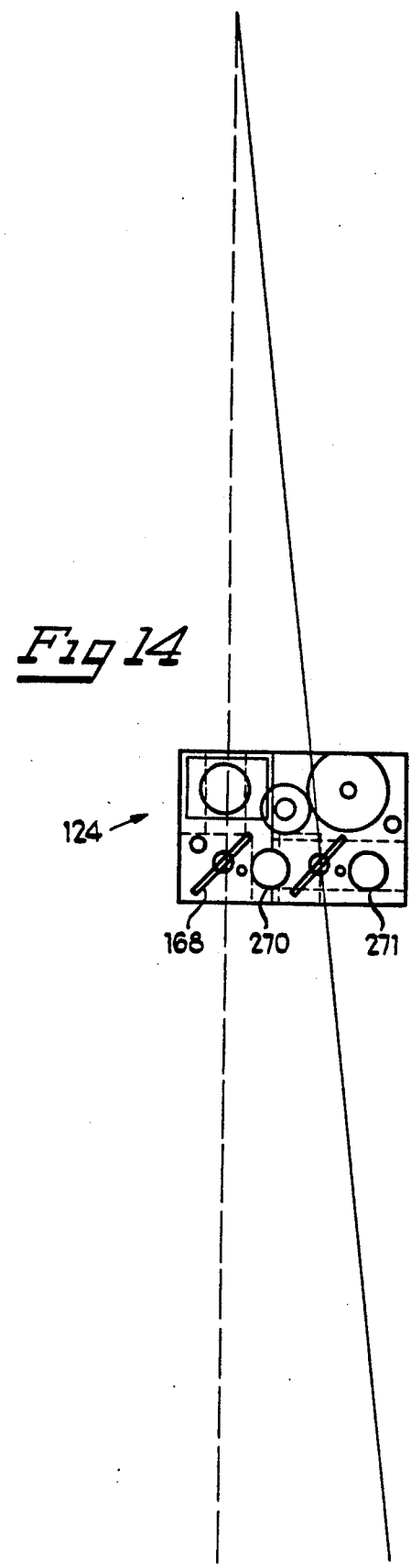
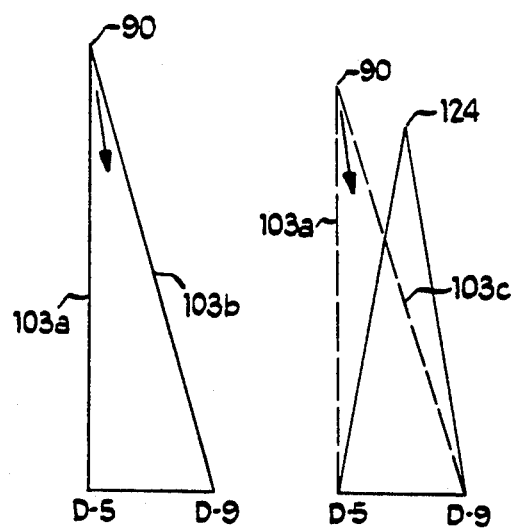

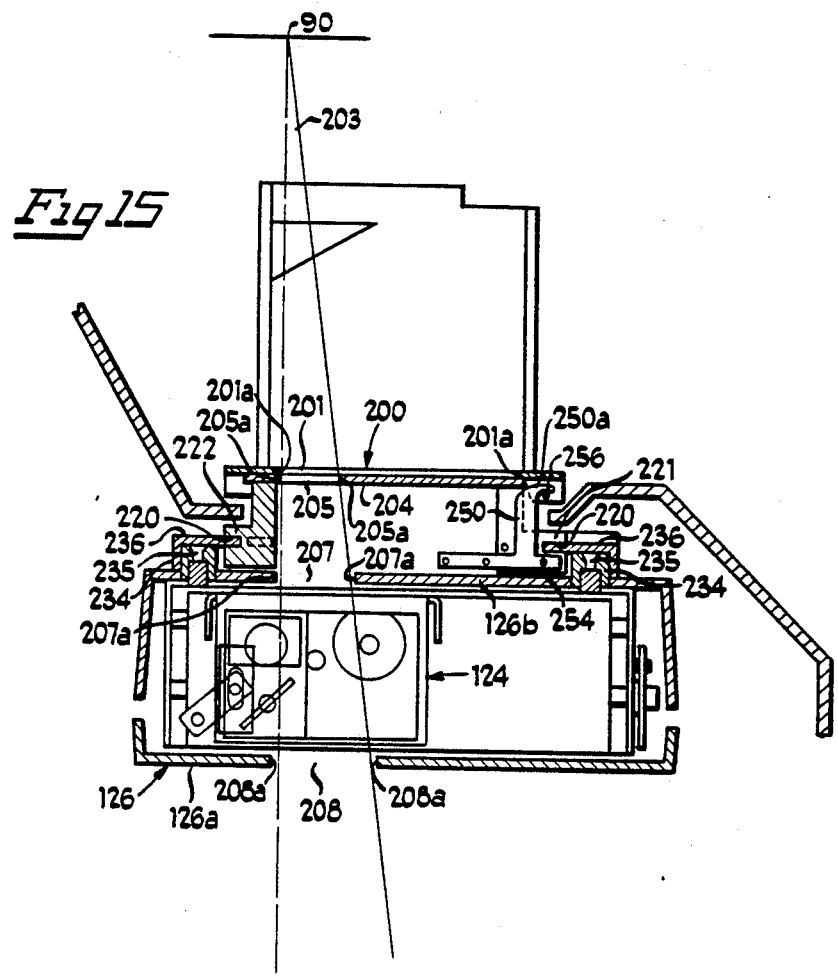
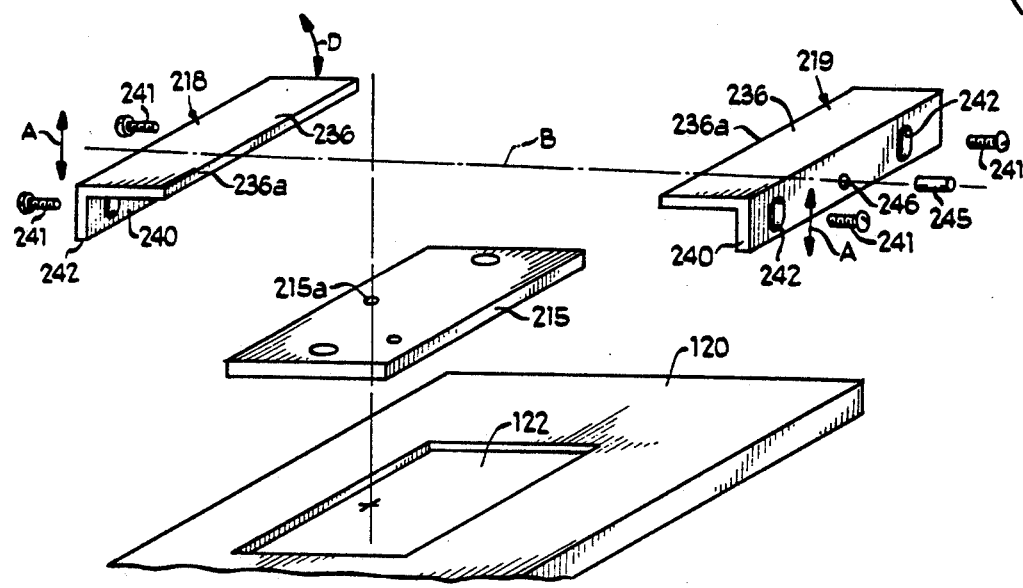

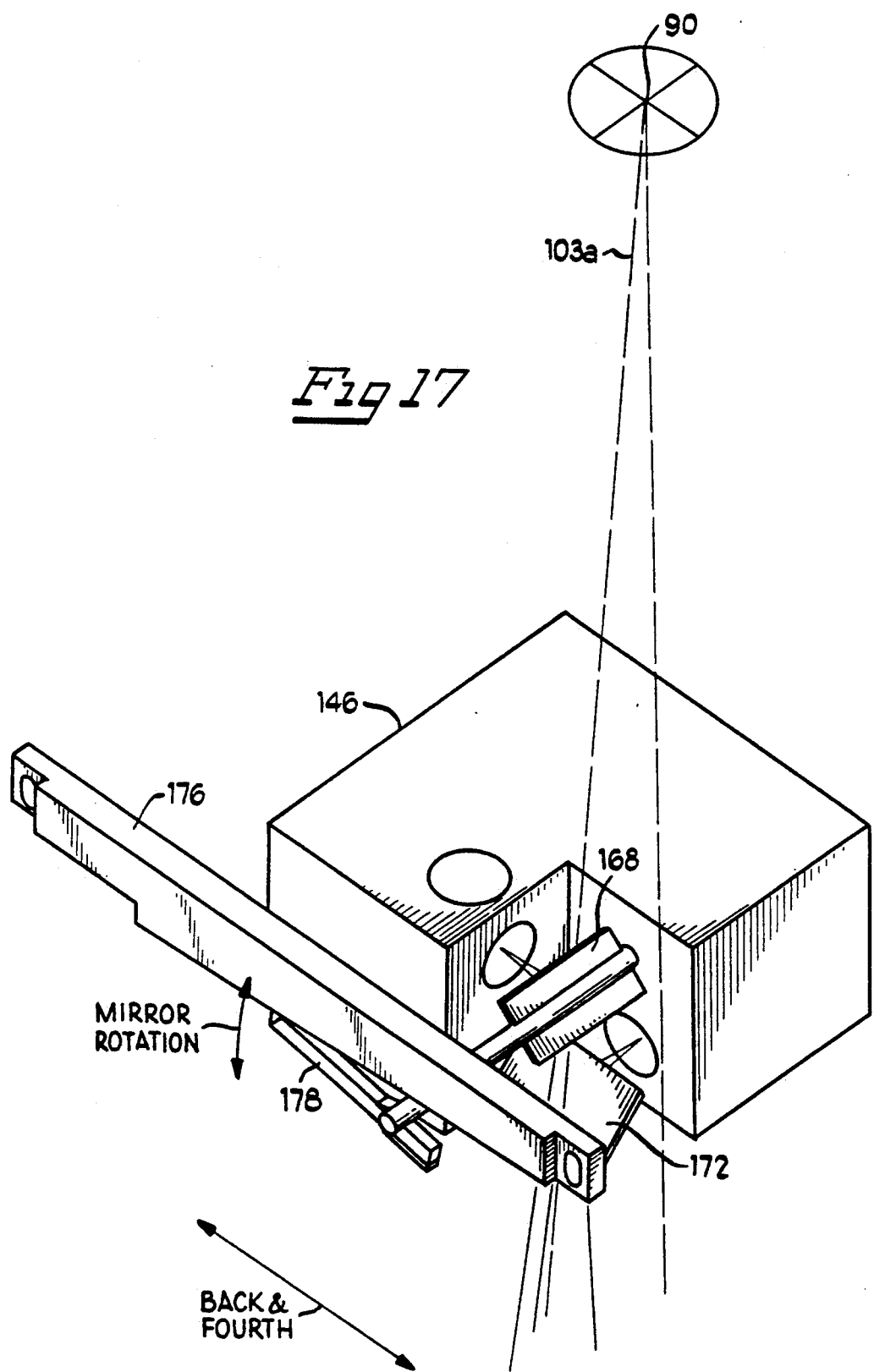

LIGHT BEAM LOCATOR AND GUIDE FOR A BIOPSY NEEDLE

This application is a continuation-in-part application of an application entitled Biopsy Locator ana Guide, Ser. No. 831,215, filed Feb. 7, 1992 still pending.

The present invention relates to an instrument for use in guiding and directing a tool such as a biopsy needle along a predetermined path, and more specifically relates to apparatus for projecting a light beam to define the path to guide the tool, e.g., to guide a biopsy needle to the lesion.

BACKGROUND OF THE INVENTION

The present invention will be described in connection with its preferred use, and that is to guide a biopsy needle during its insertion into human tissue to reach a lesion such as in a breast. The invention is not limited to this one use as it may be used in other instances, e.g., the X-ray of a fractured bone and provision of a locating and guiding beam to guide the proper angularity of a screw being threaded into the bone at a precise location and angle to secure bone fragments or a prothesis in a proper position.

In recent years the public has become very aware of the importance of X-ray examination of women's breasts in the control and cure of breast cancer. The early detection of cancerous tumors is recognized as significantly improving the chances of successful treatment. As a consequence, women of a certain age or genealogical background are subject to X-ray examination of their breasts at frequent intervals. Such examination often detects tumors or lesions which are of a questionable character, it being impossible to determine from the X-ray whether the tumor or lesion is malignant or benign. In such situations, it is normal to take a specimen or biopsy of the tumor or lesion to permit a careful examination of the abnormal tissue.

The most common means of taking a biopsy of a tumor or lesion in a woman's breast is a stereostatic device which uses an elongated needle which may be inserted with a rotary movement to cut a core sample of tissue in the area of the tumor or lesion. The needle is equipped with suction means to aid in extracting the cylindrical section of tissue. Since the current trend is toward early detection through frequent examination, the tumor or lesion which is to be checked through the biopsy is often very small and barely discernable on the X-ray. With the tumor or lesion often being well below the skin surface, it is extremely difficult to insert the biopsy needle with sufficient accuracy to engage and sample the area of tissue that is of interest and requires further testing.

In the presently used procedure, the breast of the patient is compressed against a horizontal surface below which the X-ray film is positioned. The compressing member is placed above the breast, clamping it against the surface, leaving a panel of skin exposed through a rectangular opening which has indicia on the sides of the opening to aid in establishing the location of the tumor discovered on the X-ray. By establishing the coordinates of the location of the tumor from the X-ray, a mark is placed on the location on the exposed skin using the indicia beside the opening to show where the biopsy needle should be inserted. An additional X-ray is taken to show the depth of the tumor so that the needle may be inserted and the specimen taken at the proper depth below the skin surface. After a biopsy specimen has been taken, another X-ray is taken to assure that the biopsy specimen is from the suspected tissue.

Because of the limited size of the tissue to be sampled and the possible errors in correlating the location of the needle insertion with the location of the tumor as shown on the X-ray, it is not unusual for many needle insertions to be required before achieving the proper location of the needle with respect to the tumor. The procedure causes considerable pain and discomfort and the prolongation resulting from the techniques employed suggest that improved techniques are required.

One attempt at locating the biopsy needle more precisely with respect to an X-ray picture of a tumor has involved the use of movable cross wires to create a shadow produced by an incandescent lamp to locate the needle insertion point on the skin. This technique has not proven to be particularly helpful, since the shadow image of the wires was not sharp enough to give a precise location and the normal ambient light in the area was usually too high to permit good visibility of the shadow image of the wires.

Another approach involved use of a laser dot which was projected in from the side to spot the needle insertion location on the skin. The angle at which the laser beam was projected tended to introduce errors since any deflection of the skin would cause the laser spot to shift location.

Another problem associated with biopsy is the difficulty of inserting and guiding the needle at the correct angle so that the needle tip is not displaced to a side of the tumor when the needle is inserted to the proper depth. The coordinates of the position of the tumor are determined from an X-ray beam that is usually located twenty inches or so above the X-ray film located beneath the breast. Herein, the X-ray beam emanates from an X-ray source that may be considered a point source because the X-ray beam that expands in size as it travels to X-ray film. At one particular location, e.g., usually at a coordinate designated D-5, the X-ray beam is directly vertical over the coordinate and the beam is perpendicular to the underlying X-ray film. A tumor located at D-5 will be hit by a needle located at the D-5 coordinate and guided perpendicular to the film and along a true vertical line. In such a system, when a breast tumor is located at the rear corners of the opening in the paddle, the X-ray beam from the point source may be at an angle of 3° to 5° with respect to the vertical. If the needle tip is inserted only along a true vertical plane, there is a chance that the needle tip may be displaced at an angle from the tumor missing the tumor, and this may necessitate the taking of another sample. Needless to say, such misses can be painful; and the uncomfortable position of the patient may be needed to be maintained considerably longer than necessary if the angle of needle insertion had been the same as the angle of X-ray beam. The lesions can be very small so that the missing of the lesion can occur quite easily.

In the aforesaid patent application, a continuous mark in the form of a cross or cross hair was generated from a unit located about six inches away from the X-ray point source. While the instrument disclosed in this application was a vast improvement over the conventional equipment, and has been used satisfactorily, the present invention is directed to the elimination of parallax that might be present in such devices. That is, the present invention eliminates the difference in apparent direction of the tumor, as seen from the X-ray point source on the one hand, and the laser source for the cross hair mark on the other hand. More specifically, the laser source is moved to eliminate parallax and to guide the needle along the angle and to the position of the tumor to assure that the needle is inserted at the same angle as the X-ray beam from the X-ray point source. Thus, when a second X-ray is taken, it should verify that the biopsy sample is taken from the tumor previously located for sampling.

SUMMARY OF THE INVENTION

The present invention involves method and apparatus for guiding a tool or member such as a biopsy needle into tissue or a screw into a bone along a predetermined angular path and/or to a specific location that was previously located by an X-ray of tissue or bone. The present invention, although not limited to the specific use of obtaining a biopsy specimen, is described herein in connection with the obtaining of a biopsy specimen after having identified a tumor or lesion through X-ray examination. The X-ray machine in connection with which the invention is used has an X-ray head supported above a specimen supporting platform with means provided to immobilize or clamp the specimen to be examined, as for example a woman's breast, against the platform. An X-ray film is disposed on the platform so that the X-rays radiated from the X-ray head pass through the specimen and provide an image of the specimen on the film. When a possible cancerous tumor or lesion is noted in the X-ray, it often becomes desirable to take a biopsy for further testing to ascertain the nature of the tumor. In order to take the biopsy, it is necessary to identify on the patient's skin exactly where the biopsy needle should be inserted to engage the tumor or lesion observed on the X-ray.

In the method and apparatus of the present invention, a light source generates a light beam at a controlled angle to guide the tool along a path coincident with the path of the radiated X-ray beam from the X-ray source through the lesion and to the underlying X-ray film. The preferred light source comprises a pair of laser sources which are detachably mounted between the X-ray head and the specimen platform to provide two aligned intersecting laser beams that are directed along the same common axis as the radiated X-rays. The laser beams are focused to be visible on the surface of the X-rayed specimen as a pair of lines which intersect at 90° to each other. The laser sources are mounted on a carriage which is movable along one path parallel to one of the lines and along another path parallel to the other line. Thus, by moving the carriage along either of two mutually perpendicular paths, the location of the intersection of the lines formed by the laser beams may be moved to any desired location. The clamping means or plate, which overlies the specimen platform and clamps the specimen, is formed with a rectangular opening in which a portion of the specimen is exposed. The specimen is disposed so that the tumor or lesion to be biopsied lies under the skin which is exposed through the opening in the clamping means. In order to insert the biopsy needle accurately, it is necessary to provide a marking or indication on the exposed skin as to where the biopsy needle should be inserted to engage the tumor or lesion indicated by the X-ray. A scale is used to establish the coordinates of the tumor location in the clamping means opening. These coordinates are then used to position the laser beam lines intersecting at the location on the skin above the tumor.

The laser beams are generated by diode lasers generating an oval dot which is directed through a cylindrical lens to expand the beam to form a line which is reflected from a mirror onto the specimen. The beams as they are directed toward the specimen are substantially coaxial, appearing to emanate from a single source. The laser source closest to the specimen is reflected by a beam splitter which only reflects 50% of the impinging beam. The beam from the laser source more remote from the specimen is first reflect by a mirror and that beam is directed through the beam splitter toward the specimen, with 50% of the beam passing directly through the beam splitter and to the specimen and 50% being reflected. This results in the two beams being coaxial and intersecting as they pass from the beam splitter to the specimen. Preferably, the laser head containing the two laser sources is detachably mounted directly in line with the X-ray head so that the laser beams engage the specimen along the same general path as the X-rays.

One problem in using laser beams to target or locate a position on the skin for inserting a biopsy needle is the fact that the laser beams may reflect from the clamping means into the eyes of the person using the instrument or the patient on whom it is being used. Accordingly, the laser beams may be provided with compensation means that redirects the beams as the laser supporting carriage is traversed so that the locating lines on the specimen remain on the exposed portion of the skin within the opening in the clamping means. Cams are provided so that as the carriage traverses in either of the two orthogonal directions, the mirror and the beam splitter are adjusted to maintain the centering of the laser lines within the opening in the clamping means.

The elements of the laser sources, including the diode lasers and the lenses as well as the mirror and beam splitter, are all mounted in a single Delrin block which forms the major portion of the movable carriage. The block provides a vibration-free and dimensionally precise means of mounting the laser sources and the adjustable mirror and beam splitter. Drilled pockets receive the diode lasers and the cylindrical lenses. Drilled holes are provided to receive axles that pivot the mirror and beam splitter and to receive guide rods for mounting the block for transverse movement.

The carriage providing the movable mounting for the laser sources includes an inverted U-shaped frame mounted for what will be termed front-to-back movement. The carriage frame supports the Delrin block for left/right movement with respect to the frame. Reversible motors are provided to drive the block with respect to the carriage and the carriage with respect to the laser head to position the laser sources and the laser beam lines with respect to the specimen or the opening in the clamping means.

The visible lines produced by the laser beams on the skin of the specimen are focused to have a width of 0.020 inches located about 18 inches from the laser source. Under the typical clamping pressure of about 30 pounds, the breast of the patient would typically space the clamping means from 1 to 3 inches from the supporting platform. The flesh of the specimen tends to bulge upwardly through the opening in the clamping means, making it difficult to fix the location on the skin with the coordinate location of the tumor or lesion as obtained from the X-ray. However, the laser beam line extends to a point adjacent the indicia on the edge of the opening, facilitating the alignment of the laser beam lines with the proper coordinate location.

Once the laser beam lines have been properly located by movement of the carriage with the motor drives, the intersection of the lines is used as the location for inserting the biopsy needle into the skin. Since the needle is about 0.090 inches in diameter, an incision is normally made before inserting the needle. The needle is connected to a source of suction to withdraw a cylindrical core or sample. The angled end of the needle is sharpened but must be rotated as it is inserted to cut the specimen to be removed. It is difficult to maintain the needle at a desired angle as it is inserted while rotating at the same time. Any deviation from this desired angle tends to introduce an error, since the insertion location is predicated on going downwardly to the tumor or lesion location at the desired angle.

A problem like that of parallax arises because the X-ray source is located in the X-ray head located above the laser head unit, which is attached to the bottom of the X-ray head. The X-ray source generally is a point source that generates an X-ray beam that is controlled by a diaphragm in the X-ray head. For example, a rectangular beam pattern, with a portion of the X-ray beam is directed straight downwardly at one coordinate position, e.g., C-1 and with the other portions of the X-ray beam at different coordinates having an inclination relative to the vertical. At the farthest locations from D-5, which are at coordinates A-1 and A-9 in this instance, the angle has the greatest inclination to the vertical. Thus, a lesion at a coordinate position A-1 or A-9 will be on a line drawn from the X-ray source to the film which line is at an angle to the vertical. The laser head on the other hand travels to a coordinate position directly over the lesion and directs a true vertical light beam down onto the skin at the coordinate position where the incision is to be made and provides a continuous guiding light on which the needle is centered when it is inserted. At the D-5 coordinate position, both the X-ray beam through the lesion and light beam are coincident; but at other coordinates, such as A-9, the X-ray beam through the lesion may be at 3° or more to the vertical and the laser light beam should no longer be vertical, as the tip moving into the breast may miss a small lesion or is not at spot desired because of these different angularities. This is or is akin to a parallax error.

In accordance with the present invention, the problem of parallax is eliminated by aligning the light beam with the X-ray beam at a predetermined location or coordinate position and then having a shifting means which shifts the light beam as though it emanates from a point along the path that the X-ray beam took through the lesion. In the preferred embodiment, the X-ray beam and light source are calibrated initially at a selected coordinate position, e.g., D-5 by having the X-ray beam go vertically through a calibration opening in a calibration plate and adjusting the light source and thereby the light beam until it is vertical and shines through the calibration opening in the calibration plate while the laser head is at the same D-5 coordinate position. The greatest angularity from a D-5 position for the X-ray is at the rear corners of the window in the paddle. The light beam is shifted by either rotating the mirrors, or the light source is shifted by cams so that the light beams are along a path from the X-ray point source through the lesion to the X-ray film. Thus, when one guides the tool such as a biopsy needle along this angle with the cross hairs centered on the upper end of the needle, the needle will travel into the flesh at the same angle as the X-ray beam traveled through the flesh and lesion to reach the film. Thus, the needle tip should be within the lesion when inserted to the proper depth.

The preferred light source for generating the visible guiding and locating beam is movable within the device to a position out of the path of the X-ray beam so that the X-ray beam may be shot through the openings in the device to take an X-ray to assure that the biopsy being taken is at the lesion. Preferably, the light source is driven to a home position such as a zero coordinate position, and a safety switch is actuated by the light source to assure that it is home when the X-ray source is actuated.

Thus, it will be seen that the nature of the laser beam is such that it provides a sharp, well defined line of light at the surface of the specimen and also at a level 10 inches above where the upper end of the biopsy needle terminates. It is therefore possible to use this extended intersection of the laser beams to establish a line along which the biopsy needle must move to properly engage the tumor. After the tip of the needle is located and engaged with the skin, the intersection of the laser beam lines is positioned on the outer end of the needle in an axially aligned location to assure that the needle remains at the controlled angle as it is rotated and forced downwardly into the specimen. As long as the axis of the needle is maintained centered on the intersecting beams, the controlled angularity of the needle will be maintained. The fact that the intersection of the beam emanates along the line of the X-ray radiation assures that the biopsy needle will be inserted accurately at the surface of the specimen and will move inwardly to engage the tumor or lesion. As long as the coordinates or the tumor are taken accurately from the X-ray image, the apparatus and method of the present invention provides a completely reliable method of obtaining a biopsy of a tumor or lesion located on an X-ray.

Accordingly, it is an object of the present invention to provide an improved method and apparatus for locating an insertion point and guiding a biopsy needle to engage a tumor or lesion, the location of which has been established by an X-ray.

A further object of the present invention is to provide a laser beam locating and guiding means for use in taking a biopsy of an X-rayed specimen, the means being removably mounted on the X-ray machine between the X-ray head and the specimen.

It is a further object of the present invention to provide an improved laser beam locating and guiding means for directing the guiding and locating beam at a predetermined angle to eliminate parallax.

These and other objects of the invention should be apparent from the following detailed description for carrying out the invention when read in conjunction with the accompanying drawings.

BRIEF DESCRIPTION OF THE DRAWINGS

FIG. 3 is a front perspective view from below of the carriage which supports the laser beam sources for the laser beam head;

FIG. 4 is an exploded perspective view of the laser diodes and their supporting block;

FIG. 9 is a diagrammatic view of an alternative embodiment of the invention;

FIGS. 10a, 10b and 10c are schematic diagrams of the action of the laser beam control by the alternative embodiment of FIG. 9;

FIGS. 11, 12 and 13 are schematic diagrams of the action of X-ray and light beams and the problem of parallax;

FIG. 14 illustrates a still further embodiment of the invention to eliminate parallax;

FIG. 15 illustrates a preferred embodiment of the invention;

FIG. 16 is an exploded view of the manner of calibration adjustment of the laser head of FIG. 15 to the X-ray beam;

FIG. 17 is a diagrammatic view of a cam and cam follower for adjusting the laser beam to be coincident with an X-ray beam through a lesion;

DETAILED DESCRIPTION OF THE PREFERRED EMBODIMENTS

Figure 1:
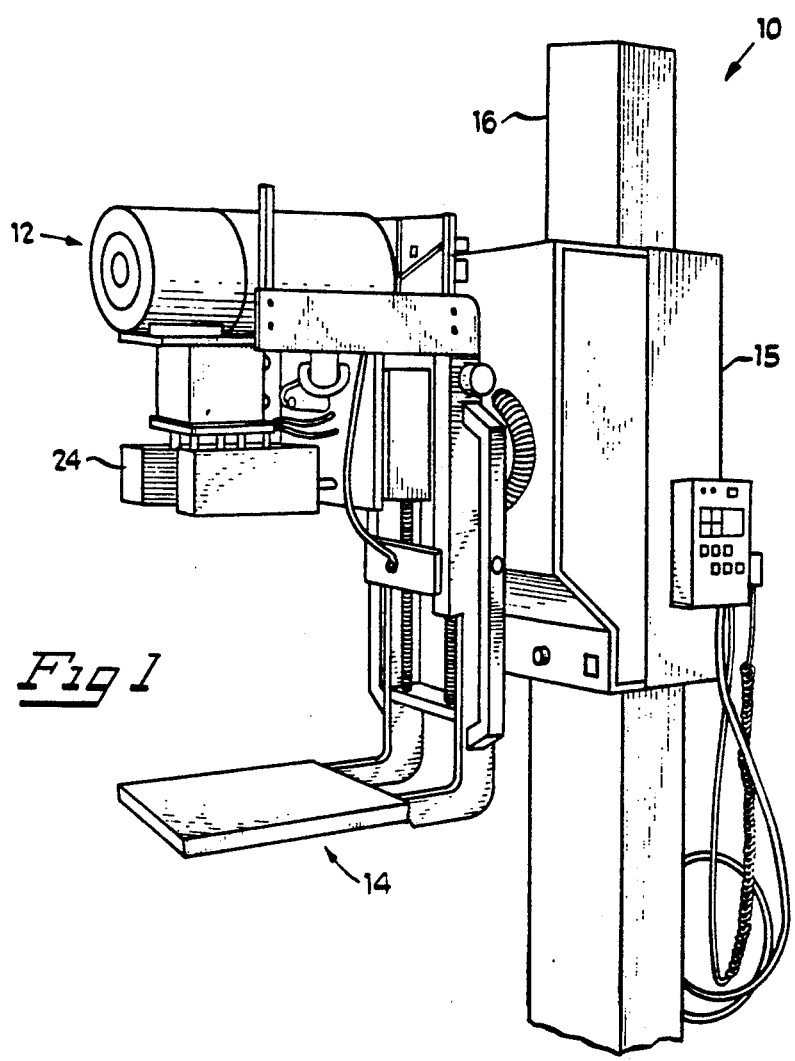
FIG. 1 is a perspective view of an X-ray machine equipped with a laser beam head embodying the present invention.

Referring to FIG. 1 of the drawings, there is shown an X-ray machine 10 which may take the form of any commercially available machine used for diagnostic examinations of the female breast as in mammography. With the recognition of the importance of early detection of cancer in improving the chances of successful treatment, there is increasing use of such X-ray machines in early detection of cancerous tumors or lesions. When such tumors or lesions are noted on X-ray images, it is usually necessary to take a biopsy of the tumor or lesion for further testing to determine the nature of the treatment that should be given to minimize the risk to the patient. Because of the small size of the tumors or lesions in this early detection stage, it is often difficult, time consuming and painful to the patient to obtain the desired biopsy of the tumor or lesion.

The X-ray machine 10 includes an X-ray head 12 from which the X-ray radiation takes place. The radiation is directed toward a support platform 14 which is adjustable in height to support the specimen to be examined, such as a female breast. The machine 10 is provided with a support column 16 and a body portion 18. The platform 14 includes means for disposing the X-ray film beneath the specimen so that when exposed to X-ray radiation from the head 12, an image of the specimen is produced on the film. The illustrated machine 10 is commercially available from Instrumentarium Imaging Corporation of Finland. Manifestly, X-ray machines of other companies may be used with the present invention.

Figure 2:
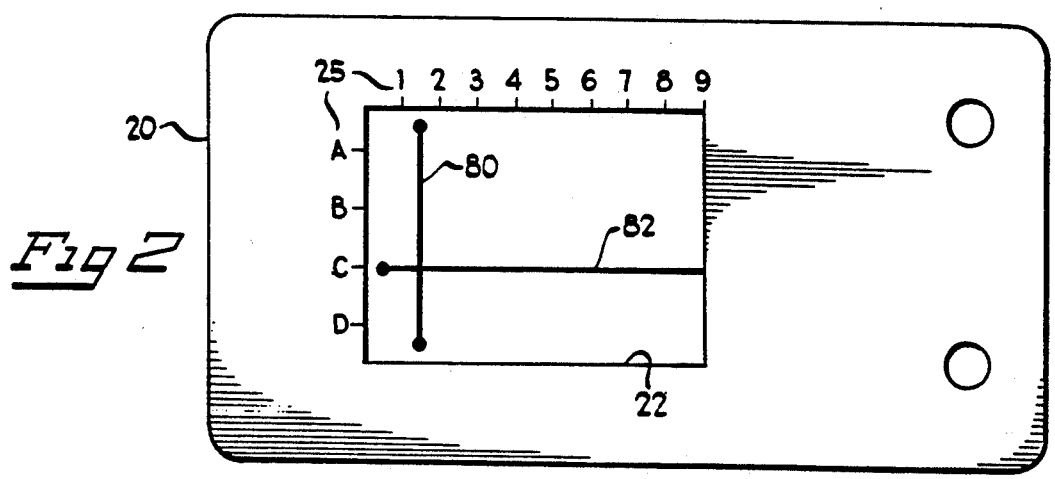
FIG. 2 is a plan view of a clamping plate of the type used in X-ray examination of the female breast.

In order to immobilize and clamp the specimen during the X-ray examination, it is common practice to use paddle or clamping means 20, as shown in FIG. 2. The clamping means 20 is mounted in parallel spaced relation to the support platform 14 and is adapted to apply a pressure of on the order of thirty pounds to the specimen during the initial X-ray examination. The pressure is reduced substantially during the biopsy. In the examination of a female breast, the clamping means 20 would be spaced 2 to 7 cm from the upper surface of the platform 14. To expose a portion of the specimen so that a biopsy may be taken by a biopsy needle 21, the clamping means 20, often called a "paddle", is formed with a opening 22 which is usually in the shape of a rectangle. At the edges of the opening 22 there are indicia 24 which permit the designation of locations with the opening 22 by coordinates such as C-1.5, indicating a location aligned with the letter C and the number 1.5. It is known to use such a clamping means provided with this type of indicia to locate a tumor from which a sample is to be taken by a biopsy needle. These clamping means are conventional in the art and need not be described in detail herein. The method and apparatus of the present invention provides a more accurate means of locating such a tumor and performing a biopsy than is now possible with presently known methods and apparatus.

The X-ray machine 10 is provided with means for detachably mounting a laser head 24 immediately below the X-ray head 12 so that the laser beams are radiated substantially along the same axis as the X-rays radiated toward the platform 14. As will be described in connection with a second embodiment in FIGS. 11-19, the X-ray emanates from what is considered a point source at a location about 20 inches above the X-ray film which is located beneath the paddle. The second embodiment is directed to eliminating parallax so that the biopsy needle is directed along a controlled angle from the X-ray point source to the lesion, as will be explained in greater detail hereinafter.

Figure 6:
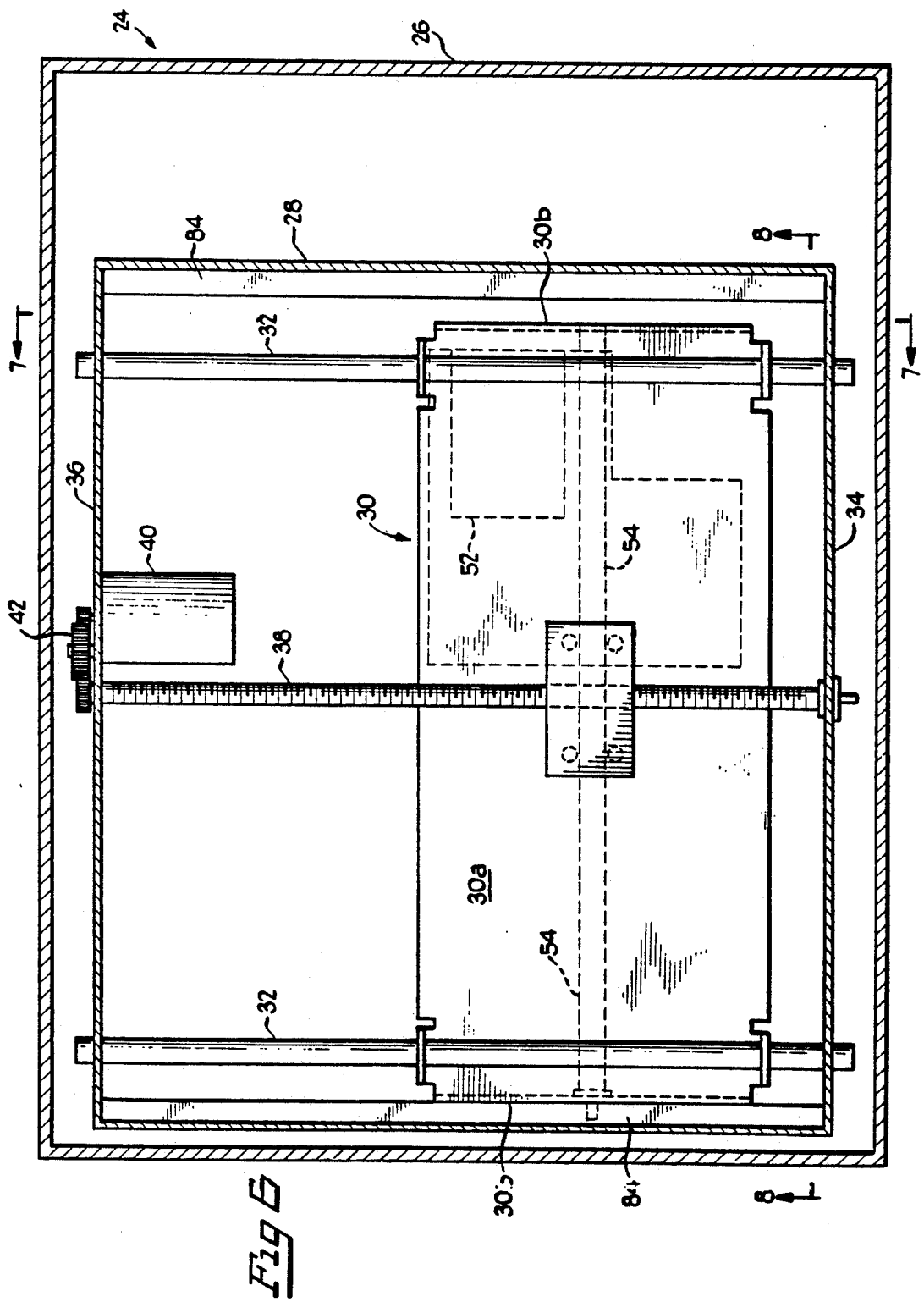
FIG. 6 is a top plan view of the laser head with the top wall cut away for illustrative purposes.
Figure 7:
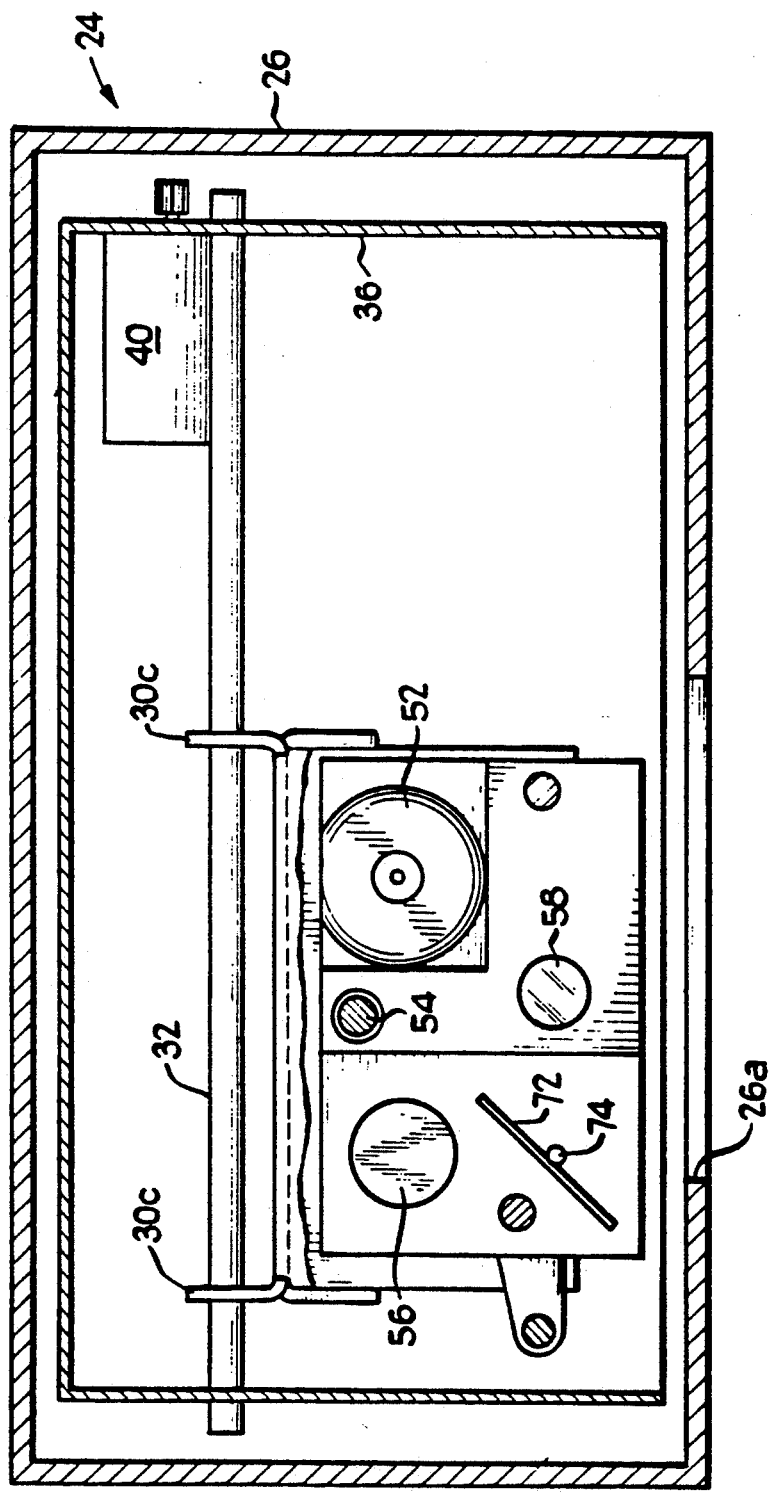
FIG. 7 is a sectional view of the laser head taken on line 7—7 of FIG. 6.
Figure 8:
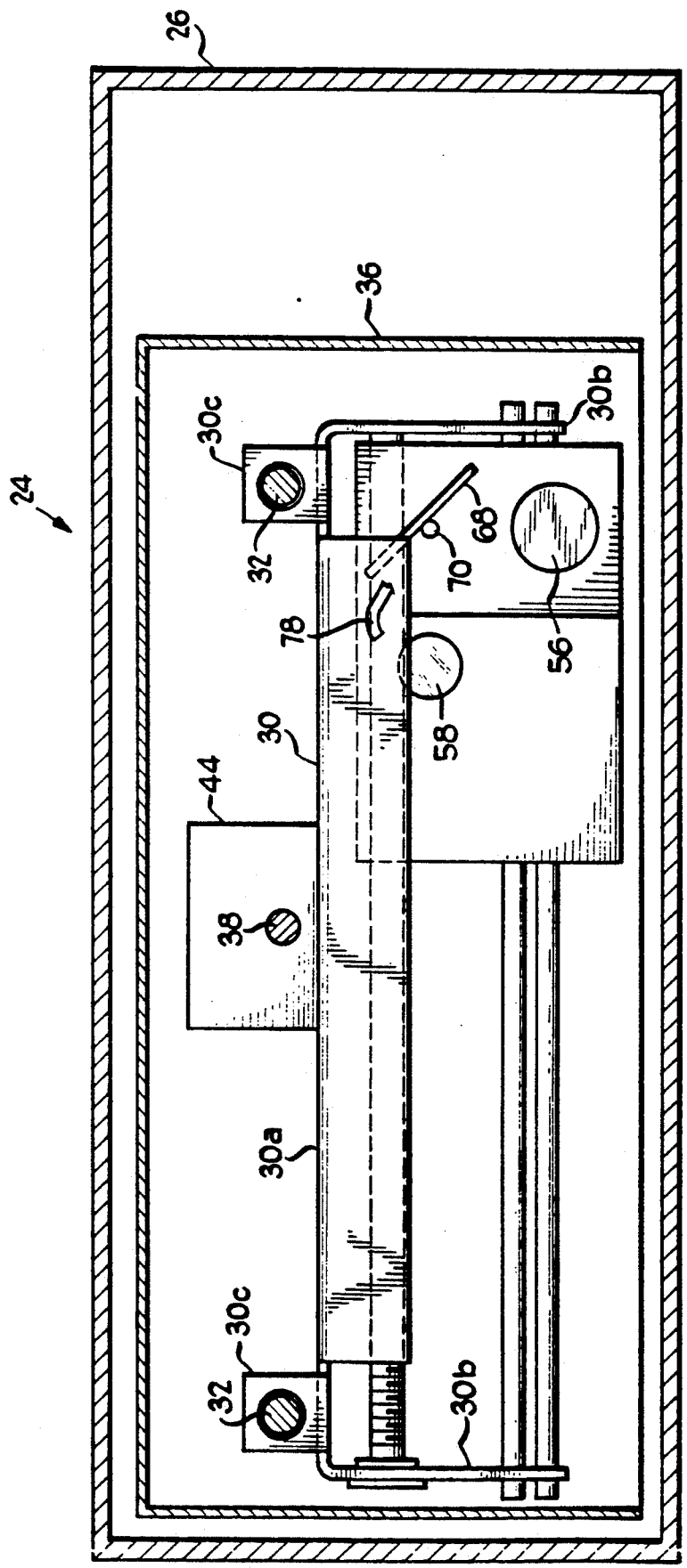
FIG. 8 is a sectional view of the laser head taken on line 8—8 of FIG. 6.
Figure 18:
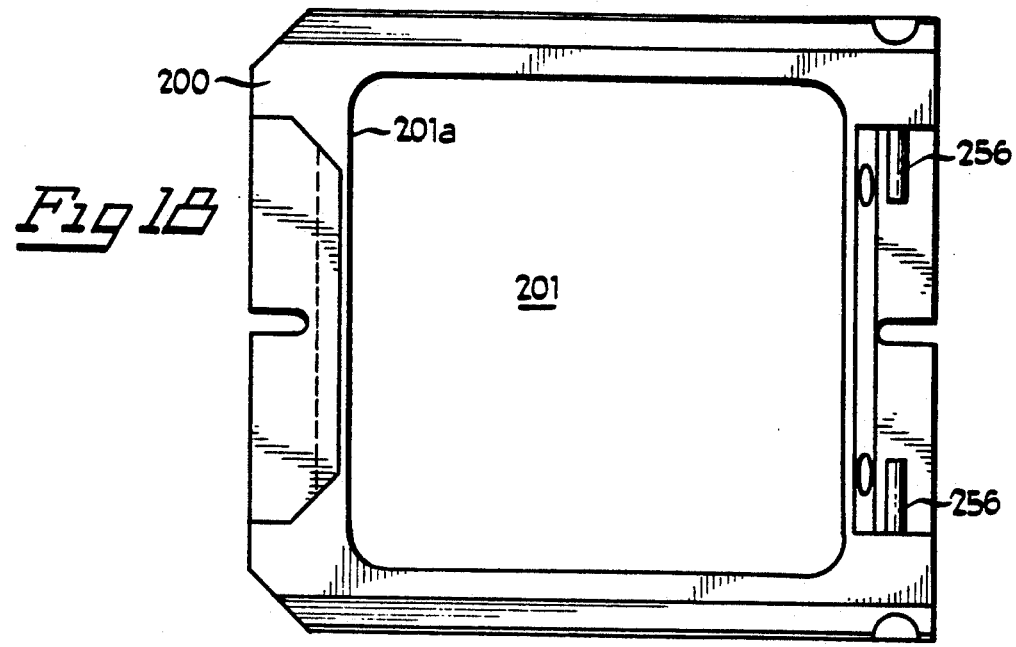
FIGS. 18 and 18a are views of a bottom diaphragm plate of an X-ray machine.
Figure 18A:
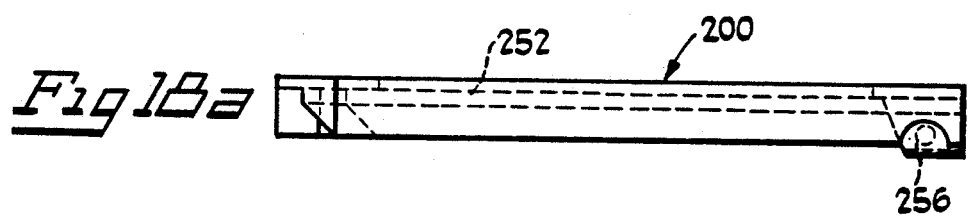
Figure 19:
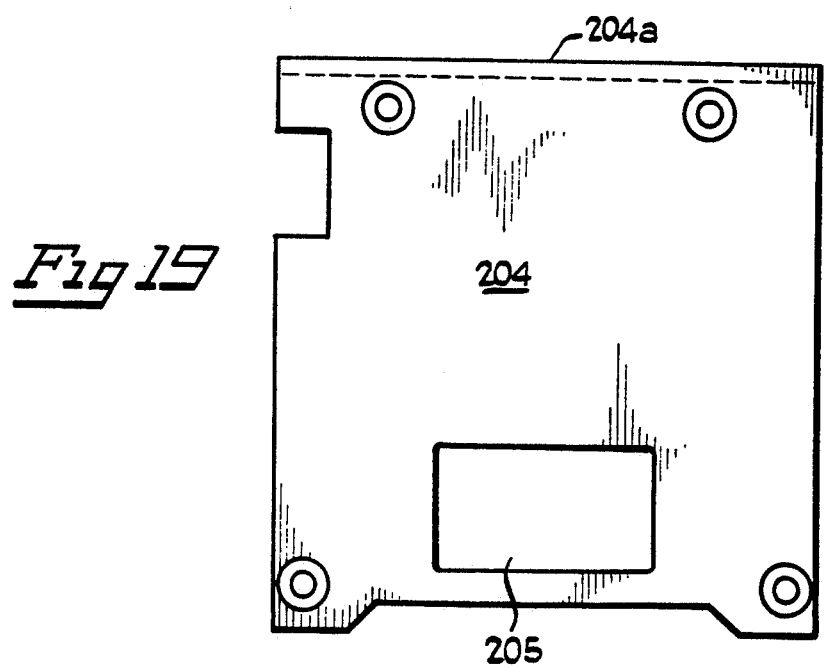
FIG. 19 is a view of a top plate for attachment to the bottom plate of the X-ray machine.

As shown in FIGS. 6-8, the laser head 24 is enclosed in a housing 26 which has closed an opening 26a in its bottom wall, as shown in FIG. 7. The opening 26a is for the purpose of allowing laser beams to be directed from within the housing 26 downwardly onto a specimen on the platform 14. Within the housing 26 there is secured a frame 28 which supports a movable carriage 30. The carriage 30 is supported and guided for horizontal movement by a pair of spaced parallel rods 32 secured to opposed front and back walls 34 and 36 respectively of the frame 28, as shown in FIG. 6.

The carriage 30 is of generally inverted U-shaped configuration having a central portion 30a which extends across beneath the rods 32 and terminates at depending sidewalls 30b. As shown in FIGS. 3 and 8, the carriage 30 is formed with upwardly extending ears or tabs 30c which mount bearings for supporting the carriage for sliding movement along the rods 32. In order to traverse the carriage forwardly and backwardly along the rods 32, a threaded feed screw or shaft 38 is provided between the rods 32 and journaled for rotation in the walls 34 and 36, as shown in FIG. 6. The feed screw 38 is rotated by a reversible motor 40 which drives the screw 38 through an idler gear 42 engaged by spur gears on the motor shaft and the screw shaft 38. At the middle of the carriage 30, there is provided a feed nut 44 which is secured to wall 30a of the carriage and which has a threaded opening to receive the screw shaft 38. Thus, as the screw shaft 38 is rotated by the motor 40, the carriage is caused to traverse along the screw 38 and the rods 32.

As is best shown in FIGS. 3 and 4, there is provided a laser support block 46 which is mounted for lateral movement with respect to the carriage 30. The block 46 provides support for the means for generating the laser beams which are used for locating and guiding a biopsy needle as will be explained in detail below. The sidewalls 30b of the carriage 30 fixedly mount the ends of two parallel guide rods 48 and 50 which extend through bored holes in the block 46. The block 46 is preferably machined from Delrin, which is self-lubricating and requires no bearings to mount the block 46 for sliding movement with respect to the rods 48 and 50. As shown in FIG. 7, there is provided a reversible motor 52 mounted on the carriage sidewall 30b to drive a feed screw 54 which engages a feed nut (not shown) on the block 46 in order to drive the block 46 along the rods 48 and 50. An idler gear and spur gears (not shown) drivingly connect the motor 52 to the feed screw 54. From the foregoing, it may be understood that the block 46 is movable laterally with respect to the carriage 30 and that the carriage 30 may traverse forward and back with respect to the mounting frame 36. This arrangement allows the block 46 to be moved front-to-back and side-to-side in a plane parallel to and spaced above the platform 14 and the clamping means 20. The block 46 provides a very inexpensive manner in which to precisely position the lasers and lenses and to maintain their positions despite a considerable handling of the apparatus during its attachment and detachment to the X-ray machine.

Supported within the block 46 are two laser diodes 56 as shown in FIG. 4. The laser diodes 56 are commercially available and are of the type producing an oval beam which may be focused to a line using a cylindrical lens 58. As shown in FIGS. 3 and 4, the block 46 has bored therein two holes 60 and 62 which receive and mount a laser diode 56 in each. Intersecting bored holes 64 and 66 receive and mount the cylindrical lenses 58. The laser diodes 56 are sufficiently recessed within the bored holes 60 and 62 to avoid interference with the lenses 58. The holes 60, 62, 64 and 66 are precision bored to snugly receive the diode lasers 56 and the cylindrical lenses 58 and to position the laser beam generating elements accurately with respect to each other.

Also mounted in the block 46 is a mirror 68 which is disposed at a 45° angle to the uppermost laser beam and which is mounted for pivoted movement about an axis 70 which lies in a vertical plane through the axis of the lowermost laser. Thus, the mirror 68 reflects the narrow beam downwardly in a vertical plane which intersects the vertical plane including the other laser beam.

Located immediately below the mirror 68 is a beam splitter 72 which will reflect 50% of the beam impinging on its surface and will pass through 50% of the beam. The beam splitter 72 is mounted for rotation about an axis 74 and is disposed at a 45° angle to the downwardly directed beam from the uppermost laser and at a 45° angle to the lowermost laser which is directed horizontally into the beam splitter 72. As a result, the beam splitter produces a downwardly directed beam which is the combination of 50% of the reflected beam from the lowermost laser and the 50% of the beam passed through from the uppermost laser. The two downwardly directed beams are intersecting and produce cross lines at the specimen or in the opening 22 in the clamping means 20.

Figure 5:
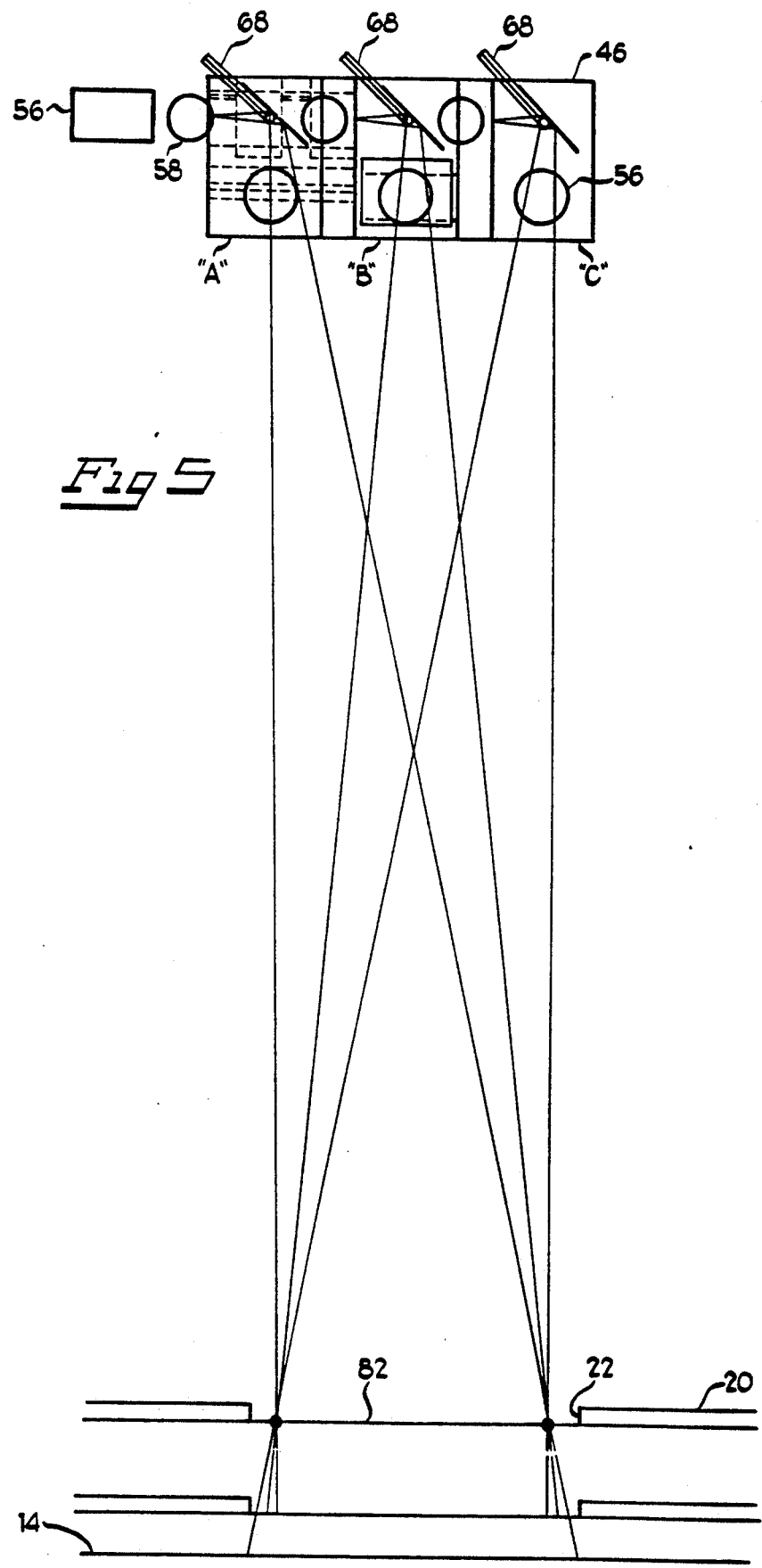
FIG. 5 is a diagrammatic view of the laser beam source in various positions illustrating the compensating mirror movement to maintain the image position fixed.

As explained above, it is important to maintain the laser beam line within the opening 22 on the clamping means 20, since reflections of the laser beam from the surface of the clamping means may be distracting and objectionable. Accordingly, means are provided in the laser head 24 to compensate for the traversing of the carriage 30 or the block 46 by adjusting the mirror 68 or the beam splitter 72 so that the laser beam lines stay within the opening 22. The problem of eliminating such reflections is complicated by the fact that the clamping means may be positioned different distances from the platform 14 depending on the thickness of the specimen when it is compressed by the clamping means 20. As noted above, this thickness may vary from 2 to 7 cm, or a total variation of about 2 inches. FIG. 5 shows how the spread or divergence of the laser beam increases in this 2 inch space and how the traversing of the carriage 30 to position the laser beam lines in the opening 22 increases the clearance that must be provided at the uppermost position of the clamping means 20. Thus, the relative positions of the laser diodes 56 and lenses 58 are selected so that the laser beam lines are slightly less in length than the length and width of the opening 22 in the clamping means 20.

Referring to FIG. 3, there is shown the compensating means for the mirror 68 which includes a laterally extending sloping cam 76 which is secured to a wall 30d of the carriage 30. A cam follower 78 extends from the mirror 68 and serves to rotate the mirror 68 about its mounting axis 70 as the block traverses laterally with respect to the carriage 30. This rotation of mirror 68 movement thus causes the right-to-left extending line to stay within the opening 22 as the front-to-back line is moved across the specimen or target area. This action of the cam 76 and follower 78 is best illustrated by reference to FIG. 5.

Shown diagrammatically is a portion of block 46 supporting mirror 68 in three different positions, illustrating how the mirror adjusts the beam as the block 46 traverses laterally to reposition the other (front-to-back) beam. In the position designated as "B" in FIG. 5, the block 46 is centrally located with respect to the carriage 30, positioning line 80 in FIG. 2 at the "5" mark or in the center of the left-to-right scale. In the "A" and "C" positions shown in FIG. 5, the block has traversed to the left and right, respectively. The action of the cam follower 78 on the cam 76 causes the right-to-left line 82, as shown in FIGS. 2 and 5, to remain within the opening 22. In the position "A" from FIG. 5, the line 80 (front-to-back) would be to the left edge of the opening 22, as shown in FIG. 2.

The compensation means for the beam splitter 72 is similar to that provided for the mirror 68. A pair of cams 84 are mounted on the inside walls of the frame 28, as shown in FIGS. 3 and 6, and extend in parallel spaced relation to the sidewalls 30b of the carriage 30. Coupled to the beam splitter 72 along the pivot axis 74 is a cam follower lever 86 which is engaged with a cam follower bar 88, as shown in FIG. 3. The bar 88 is supported for swinging movement against the underside of the cams 84 by links 90. Thus, as the carriage 30 traverses front-to-back, the bar 88 rides against the cams 84, causing the cam follower lever 86 to rotate the beam splitter 72. This action of the cams and cam follower lever causes the front-to-back line 80 to be adjusted or redirected as the carriage 30 traverses to move the right-to-left line 82 toward the front or back of the opening 22. In this manner the line 80 is maintained within the opening and does not engage the clamping means 20, causing objectionable reflections.

It may be necessary on some occasions, such as during initial set-up of the X-ray machine and attachment of this invention thereto, to initially center the lines 80 and 82 within the opening 22 of the clamping means 20. For this purpose, there are provided externally accessible adjustment means for the cams 76 and 84. Suitable positioning of these cams can be used to properly position the lines 80 and 82 within opening 22. In FIG. 3 there is shown an adjustment means 92 for the cam 76 as an example.

Shown in FIG. 9 is an alternative embodiment of the invention wherein the compensating means for directing the laser beams during traversing of the laser beam sources constitutes movable shutters, rather than the pivotal movement of the mirror and beam splitter. As shown in FIG. 9, a cam 100 is positioned adjacent the carriage which supports a laser diode 102, a lens 104, a mirror 106 and a cam follower 108. A shutter 110 is mounted on the carriage beneath the mirror 106 for movement in the plane of the carriage movement along a path aligned with the plane of the laser beam. The shutter 110 has an opening 110a through which the beam is directed and which functions to define the length and position of the beam passing therethrough. As shown in FIGS. 10a, 10b and 10c, the shutter 110 functions in the same manner as the pivoting mirror in compensating for the carriage movement to maintain the laser beam within the target area.

A second shutter would be utilized in the alternative embodiment to compensate for the movement of the beam in the orthogonal direction also. Thus, there are two separate shutters and cams controlling the displacement of both of the laser beams as in connection with the embodiment of FIGS. 3-8. The laser diode 102 and lens 104 provide a beam of sufficient width to completely span the opening 22 in the clamping means 20 at the limits to which the carriage may traverse. By movement of the shutter 110 by the action of the cam 100, the shutter 110 effectively cuts off the ends of the laser beam line which would otherwise extend beyond the edges of opening 22 as a consequence of the displacement of the carriage from its central location. The other laser bean would similarly have the edges of its beam limited by the cams that had controlled the angling of the beam splitter. Either the shutter or the pivotal mirrors provide an acceptable means for limiting the laser beams to the target area within the opening 22 of the clamping means.

In the normal use of the laser head 24 and in the practice of the method of the present invention, an X-ray picture is utilized to establish the location of a tumor or lesion which is to be the subject of a biopsy. Through the use of a scale, the coordinates locating the tumor on the X-ray picture are established. Through the operation of the motors 40 and 52, the laser beam lines 80 and 82 are moved within the opening 22 to position the lines in accordance with the measured coordinates. This provides the precise location on the skin where the biopsy needle should be inserted. The two laser beams provide sharp, distinct lines which are 0.020 inch in width and may be easily seen with any ambient light conditions in the area of the X-ray equipment. The point of the intersection of the lines is created by laser beam portions projecting vertically with respect to the specimen being examined, so any bulging of the flesh through the opening in the clamping means has no tendency to introduce errors in the location of the surface point above the tumor.

Even if the surface location is toward the edge or corner of the opening 22, the intersecting beam will still be vertical in this embodiment of the invention (or at a desired angle in the second embodiment of the invention described hereinafter) and the ends of the laser beam lines will still be within the opening 22. Thus, there will be no objectionable reflections caused by the laser beams reflecting on the clamping means 20. Having established the location on the skin surface with the laser beam lines, an incision is made at the indicated location which has not been contaminated by the need to mark the skin to locate the tumor. The biopsy needle is then inserted at the point marked by the laser beam lines. Herein, the intersection line of the focused beams may be on a true vertical line or at a desired angle through the X-ray head of the machine. By aligning the biopsy needle on this true vertical or the desired angle, the lower tip of the needle will progress straight down to the lesion and not go off to the side of the lesion as occurs when the needle is tilted from the desired angle. The angular orientation of the needle is continually maintained so that the laser beam lines intersect and provide a cross with a central dot at the cross section on the upper end of the needle, along the needle axis. By maintaining the dot centered on the upper end of the needle as the needle is rotated in taking the biopsy sample, the proper angular positioning of the needle is assured. Having accurately established the skin location for inserting the biopsy needle and having maintained the angular orientation of the needle, the operator has improved considerably the likelihood of properly engaging the tumor for biopsy on the first attempt, as compared to the prior art methods which were less precise.

From the foregoing description, it should be readily understood that the present invention provides a significant improvement in the method and apparatus for performing a biopsy on a tumor or lesion which has been identified and located by means of an X-ray. The laser beam lines generated by the laser head 24 provide a means of using a coordinate location as determined from an X-ray picture to accurately establish a location on the skin of the specimen for inserting a biopsy needle, and thereafter using the laser beam lines to maintain the desired angular positioning of the biopsy needle while rotating the needle and forcing it into the specimen. By centering the axis of the needle on the intersecting laser beam lines, the needle will be properly directed to engage the tumor or lesion.

In accordance with another embodiment of the invention, which is illustrated in FIGS. 11-19, the laser head 124 is mounted so as to be movable to eliminate parallax, that is, the laser beam 101 is shifted so that the laser is at the same angle as the portion of X-ray beam 103 through the lesion at a given coordinate position so that when the tip of the biopsy needle is at the proper depth it should be in the lesion. Referring now to FIGS. 11-13, the X-ray beam is considered to emanate from a point source 90 and it is located over the X-ray film at a position in which one coordinate position on the paddle 120 and film therebelow 103a so a portion of the beam is at a true vertical, e.g., at position D-5 (FIG. 12). Hereinafter, a prefix "1" will be added to any reference character heretofore used in connection with FIGS. 1-10 when describing an element identical to or substantially equivalent to an element already described to eliminate need for duplication of description and to aid in understanding the invention. The portion of X-ray beam 103 hitting the coordinate positions A-1 or A-9 is at an angle of about 3°–4° from the true vertical. The compressed breast is usually three to five centimeters in thickness, and the lesion may be located considerably inward of the location where the laser beam strikes the breast at a given coordinate, such as an A-1 or an A-9 coordinate. Referring now to FIG. 13, the cross hair laser beam 101 emanates from the laser head 124 which is positioned about five or six inches below the X-ray source 90 and is shifted to different coordinate positions. For example, between D-5 and D-9 with the cross hair laser beam 101 is being directed straight down, as shown in dotted lines in FIG. 13. In the embodiment described in FIGS. 1–10, the needle when centered on the laser beam which was always in a true vertical position. The X-ray source 90 does not move along the coordinate positions to be directly vertical at all coordinate positions as does the laser head. Herein, only the portion 103a of the X-ray beam 103 is in a true vertical position, as shown by the line 103a in FIGS. 12 and 13; while the 103c line represents an X-ray at an angle from the true vertical.

In the present invention, means are provided to tilt the laser beam 101, for example, from its true vertical position shown in FIG. 11, to be coincident with the X-ray beam portion 103b at the coordinate position D-1 and to be coincident with the X-ray beam portion 103c at D-9 (FIG. 13). Thus, for each coordinate position, the laser beam has the same angularity as the X-ray beam. Thus, there is an angular coincidence of the laser beam and the respective X-ray beam portions at all coordinate positions to eliminate parallax so the needle tip should always hit the lesion.

Also, as will be explained in greater detail hereinafter, the unit is readily calibrated to the X-ray source and machine; and the unit is adapted to be readily attached and detached, preferably by a sliding motion of the unit horizontally to a position laterally remote from the needle so that it will never be accidentally dropped onto a needle already in a breast.

In accordance with a further aspect of the invention, there are openings or windows 205 and 207 (FIG. 15) provided in the unit through which an X-ray beam 103 may pass without limiting the beam's path. Thus, the preferred unit does not act as a diaphragm defining the shape of the X-ray beam. Also, the laser head 124 is preferably mounted so that it can be homed, that is, moved to a home position clear of the X-ray beam path so that an X-ray may be taken through the unit with the needle tip in the lesion as photo-graphic evidence that the lesion was actually hit by the needle and not missed. This housing is done by rotating the drive motors described in connection with FIGS. 1–10 to shift the carriage from the X-ray beam path.

Referring now in greater detail to the preferred embodiment of the invention, the laser unit is attached to a bottom X-ray machine plate 200 (FIG. 15), which has a diaphragm opening 201 with edges 201a which shape the X-ray beam emanating from the point source 90. The laser unit has an upper plate 204 with an upper window 205 having edges 205a that are spaced outwardly of the X-ray beam so as not to be impinged by the X-ray beam. As will be explained in greater detail, the laser unit comprises the upper plate 204 and a pair of guide blocks 221 and 222 that are detachably mounted to the X-ray machine at its bottom plate. The guide blocks 221 and 222 have horizontal grooves 220 which sliding receive the laser head 124, which is slid from and into the grooves for each patient; whereas, the top plate 204 and guide blocks remain with the X-ray machine when it is being used without the laser head 124. For example, when one is taking the initial set of X-ray photographs to spot the lesions for biopsy. This slidable laser head 124 includes the outer housing 126 which has an upper housing plate or wall 126b (FIG. 15) extending horizontally with an opening 207 through which the X-ray beam 103 passes. The edges 207a of the opening 207 are spaced at a greater distance than the X-ray beam width and the housing 126 has a bottom horizontal wall 126a with an opening 208 defined by edges 208a located outwardly of the X-ray beam. Thus, the X-ray beam passes through the entire laser unit without being restricted, thereby when it is desired to take an X-ray with the laser head 124 still on the X-ray head, the laser head carriage will be shifted out of the path of the X-ray beam within the housing 126; and it is preferred that the arrival of the laser carriage at this home position actuate an enabling switch 210 (FIG. 15) which is connected to the X-ray head control circuit. Until the switch 210 is actuated, the X-ray head cannot be activated to produce an X-ray that would hit the laser carriage or the laser head 124.

The preferred manner of eliminating parallax is to employ cams 176 and 184 similar to the cams 76 and 84 (FIG. 3), and cam followers 170 and 186 similar to cam followers 70 and 86 (FIG. 3), to rotate the mirror 168 and the beam splitter 172 to change the angularity of the laser beam 101 as the laser head is shifted in the X and Y directions. Thus, as diagrammatically shown in FIG. 17, the cam follower 178 is in the form of a lever having a shaft pivotally mounted in the block 146 for pivoting by the elongated stationary cam 176 to in turn pivot the mirror 168 which is mounted on the lever shaft. The cams are so designed that the laser beam will be inclined in the same path from the upper X-ray source 90 through the lesion for a given coordinate position. That is, the preferred means is a cam system similar in all respects to the cam system described previously to keep the laser beam from hitting the edges of the rectangular opening in the clamping means 20. It is not thought that the light reflected from the laser beam hitting the edges is a great problem; and that cams 176 and 184 are preferred to eliminate parallax, rather than using cams 76 and 84 to prevent the laser beam from hitting the edge of the clamping means 20.

In order to achieve the desired angular coincidence of the portion X-ray beam 103 through the lesion and the laser light beam 101, the laser unit 91 is first calibrated or oriented with respect to the X-ray source 90 when the laser head unit 124 is initially installed. In this instance, the laser head unit 124 is easily adjusted in the vertical direction, as indicated by the arrow A in FIG. 16, and is adapted to be rotated about a horizontal axis B. The preferred orientation involves the uses of an alignment or orientation plate 215 which is sized to fit into opening 122 in clamping means 120. The orientation plate has at least one opening or diaphragm 215a which is positioned at a specific location or coordination position, e.g., position D-5, at which the X-ray is at a known angular position, in this instance, the true vertical angular position. The laser head unit then needs to be adjusted until its cross hair laser beam 101 is also in a vertical position to shine through the aperture 215a. To achieve this vertical orientation of the laser beam, the laser head 124 is positioned over the coordinate location D-5 and then several adjustments are made, for example, the laser head unit may be shifted in the X and Y directions, rotated about the axis B, and the left side may be raised or lowered relative to the right side. Usually, within about five to seven minutes, it is possible to make these adjustments and to orient the laser beam 101 to be coincident with the X-ray beam portion 103a at the D-5 coordinate position. The cams 176 and 184 will then shift the laser beam to stay coincident with the various X-ray beam portions, e.g., 103b or 103c, and to have the same angularity for both of laser beam and an X-ray beam portion going through a lesion at any of the coordinate positions.

The preferred laser head unit is mounted for sliding movement to and from the grooves 220 in the support blocks 221 and 222; and, to this end, the laser head unit 124 includes a pair of slide flanges 218 and 219 (FIGS. 15 and 16) which slide in horizontal slide grooves 220 in the pair of slide blocks 221 and 222 each of which is secured at their upper ends to the stationary top plate 204, which is attached to the X-ray machine bottom plate 200. Herein, the side flanges 218 and 219 are fastened to the upper housing wall 126b of the housing 126 which carries the laser head carriage and motor drives therefor. The preferred manner of mounting the side flanges 218 and 219 to the housing 126 is by means of a pair of horizontal bars 234 which are secured by vertical screw fasteners 235 to housing top wall 126b. The slide flanges 218 and 219 each have an upper horizontal leg 234 resting on the top side of the bar 234 with a free edge 236a projecting inwardly beyond the bar, and received within the adjacent groove 220 in its respectively associated guide block 221 and 222. The slide flanges also have an integral vertical leg 240 to be secured by a horizontally-extending, threaded fasteners 241 projecting through vertically elongated holes 242 in these vertical legs 240, and threaded into an aligned threaded bore in an adjacent, outer side of the associated bar 234. The vertically-elongated apertures 242 are elongated sufficiently to allow the unit housing 126 to be raised or lowered relative to the slide flanges and to be tilted or rotated about an axis B through a tilt pin 245, as will be explained. After adjusting, the screws 241 are tightened to lock the flanges 218 and 219 against the bars 234 at the adjusted position.

By loosening the screws 241 in the lefthand flange 218, and leaving the pin 245 in the side flange 219 and its associated bar 234, the left side of the laser head unit may be raised or lowered relative to righthand side to give a rocking motion to get laser carriage and laser heads in a generally horizontal plane so that the laser light is truly perpendicular to the calibration plate 215 and will pass straight through the calibration aperture 215a.

In calibrating the laser beam 201 to the X-ray beam portion 103a, the laser head unit may be tilted or pivoted about the horizontal axis B (FIG. 16) on which is located the tilt pin 245. The tilt pin is a small metal pin that is mounted in righthand bar 234 and projects through a pivot hole 246 in depending leg 240 of the slide flange 219. With the four screw fasteners 241 loosened but still in the elongated holes 242, the depending housing 126 may be rotated about the tilt pin when adjusting the laser beam 101 to be in a true vertical plane to shine through the aperture 215a in the orientation plate 215. After the proper tilting, the screw fasteners 241 are tightened to clamp the vertical legs 240 of the slide flanges to the vertical sides of the bars 234. The slide bars 218 and 219 having been previously slid within the grooves 220 until the laser beam is over the D-5 coordinate and shines down onto and through the aperture 215a in the aperture plate.

The preferred manner of attachment of the whole unit to the underside of an X-ray head 112 is by means of hooks 250 and an edge 204a of the upper plate 204 inserted into and received within a groove 252 in bottom plate 200 of the X-ray head 112. The preferred hooks 250 are pivotably mounted in the righthand block 221 with hook ends 255 hooked over horizontal pins 256 fixed in the X-ray bottom plate. The preferred hooks are biased by springs (not shown) to the illustrated locking position. When it is desired to remove the entire laser unit from the X-ray machine, the hooks 250 are pivoted counterclockwise (FIG. 15) about a pivot pin 254 in the block 221 until the hook ends 250a clear the pins 256; and the top plate 204 and attached blocks 221 and 222 are slid down and to the right to the slide top plate's edge 205a from the groove 251 in the X-ray machine bottom plate 200.

In this illustrated embodiment of the invention, there are two short pins 256 (FIG. 19) mounted at spaced locations in the bottom diaphragm plate 200 of the X-ray head to receive two hooks on the unit. The unit has its top plate 204 with its window 205 with its left edge slid into the receiving groove 251 in a depending wall 258 on the diaphragm bottom plate of the X-ray machine.

The blocks 221 are secured by four threaded fasteners projecting down through apertures in the top plate 204 into threaded bores in the top wall of the blocks 221 and 222 to secure the blocks to the underside of the top plate. The top plate 204 and attached blocks 221 and 222 remain attached to the X-ray plate 112 when the laser head unit is slid from the grooves 220 in the blocks until flanges edges 236a are removed from the grooves 220. Preferably, this sliding movement is five or six inches; so that if the laser head should be accidentally dropped, it will not fall on the needle in the breast.

It will be appreciated that the cams and cam followers described herein are but one form of various means that can be used to adjust the position of the laser beam 101. For example, in FIG. 14, a pair of motors 270 and 271 may be mounted in the carriage of the laser head and rotated incrementally under computer numerical control (CNC) to rotate the beam splitter 171 and the mirror 168 through small increments corresponding to the amount of rotational movement that the respective cams and cam followers would cause. The calibration could be done with adjustments either, as above-described, or by changes caused by the computer program to adjust the mirror and beam splitter initial positions. The rotation of the mirror and beam splitter by the motors 270 and 271 will result in the cross hair laser beam being tilted at the same angle as the angle of the portion of the X-ray beam passing the lesion at a given coordinate position. Thus, by holding the center intersectional dot of the cross hair on the end of the needle as it is inserted into the breast, the needle tip will proceed along the imaginary line between the X-ray point source 90, through the lesion and to the lesion image on the underlying X-ray film.

When the laser beam 101 is used to direct other members, e.g., a screw to be threaded into hip bones to join the same together, the laser head carriage may be mounted on a curvilinear track for movement around a curved path, rather than a straight line path herein described. Of course, the invention may be used in various operations with an X-ray device, and the present invention is not limited to the particular operation of a breast tumor biopsy as described herein in detail.

Although the invention has been described with regard to various preferred embodiments, it should be understood that various changes and modifications as would be obvious to one having the ordinary skill in this art may be made without departing from the scope of the invention which is defined in the appended claims.

What is claimed is:

1. A device for locating and guiding a biopsy needle during a procedure in which a breast lesion has been identified by X-ray examination from a substantially point source of X-rays and a specimen of the lesion is to be obtained, said device comprising:

a laser head including first laser source for radiating a first focused beam in a first plane visible as a first line on the breast and a second laser source for radiating a second focused beam in a second plane visible as a second line on the breast, said beams intersecting and radiating visible as a continuous cross hair;

traversing means for moving said first laser source perpendicular to said first line and for moving said second laser source perpendicular to said second line;

means for directing toward the specimen said focused beams and their intersections as the continuous cross hair for marking an insertion location for a biopsy needle in said target area and at an angle to align the needle during insertion to the lesion; and adjusting means for adjusting said focused beams to different angles to the vertical as the laser head traverses to different angles to the vertical as the error between the laser beams and the point source of the X-rays.

2. A method of locating and obtaining a biopsy of a lesion in a specimen comprising the steps of:

clamping a specimen with clamping means in a fixed position in an X-ray machine;

radiating the specimen with X-rays to form an X-ray picture of the specimen to locate a lesion;

providing indica means associated with the clamping means for locating a lesion on said X-ray picture by means of coordinates;

generating a laser beam in a continuous cross hair pattern emanating from a location along the line of the X-ray radiation;

positioning the continuous laser beam in accordance with the coordinate locations of said lesions as shown by the X-ray picture;

adjusting the inclination of the laser beam for different coordinate locations of the lesion and directing the needle along these different inclination at each the respective locations, and applying the tip of a biopsy needle to the intersection on the specimen of the lines formed by the laser beam and taking a biopsy sample of the specimen.

3. An apparatus for locating a point of entry for a biopsy needle on a person's body and for guiding the biopsy needle to obtain a specimen which has been located on an X-ray film by an X-ray of the specimen, said apparatus comprising:

a frame for mounting on an X-ray machine for generating an X-ray from a point source;

a light source in the frame for radiating a focused beam to provide a visible beam along which the biopsy needle may be guided;

positioning means for shifting type light source relative to the frame to locate the light beam at a number of predetermined locations defined by coordinates above the specimen;

shifting means for positioning the light beam along an angle simulating the angle from the X-ray point source through the specimen at the coordinate location to the film to reduce parallax error so that the biopsy needle may be guided at the approximate angle from the X-ray point source to the specimen, the light source including a laser for generating a light beam in the form of a cross hair which is to be centered at the point of entry for the biopsy needle and as a cross hair on a distal end of the biopsy needle.

4. An apparatus in accordance with claim 3 in which openings are provided in the frame through which the X-ray beam may pass without hitting the frame, and the light source is shifted by the shifting means to a position in which the X-ray beam will not strike the light source when an X-ray is taken through the openings in the frame.

5. An apparatus in accordance with claim 3 in which the shifting means shifts the light source to a home position, and sensor means for sensing the positioning of the light source at the home position for enabling the shooting of the X-ray beam.

6. An apparatus in accordance with claim 3 including a calibrating means to align the laser beam with a portion of the X-ray beam at a predetermined coordinate position.

7. An apparatus in accordance with claim 6 in which the calibrating means includes a diaphragm to direct a vertical portion of X-ray beam as a small beam to a predetermined coordinate position; and in which the calibrating means includes an orientating means to orient the visible laser beam to the same coordinate position thereby calibrating the light beam with the X-ray beam.

8. An apparatus in accordance with claim 3 including a computer controlled drive motor means to turn the angle of the laser light beam for the different coordinate positions to align the laser beam along a path from the light source through the lesion and to the X-ray film at each of the different coordinate positions designating a lesion.

9. Apparatus for use in X-ray examination and diagnostic procedures using a biopsy needle having a hollow first end to take a sample of a specimen and having an opposite end, the apparatus comprising:

an X-ray machine having an X-ray radiation head mounted in spaced relation to a specimen supporting platform for providing a substantially point source of X-rays, a clamping plate mounted in spaced parallel relation to said platform to clamp said specimen against said platform, said clamping plate having an opening exposing a portion of said specimen;

a laser head on said X-ray machine between said X-ray radiation head and said specimen supporting platform;

first and second laser sources mounted on the laser head and radiating focused beams to provide a continuous cross hair line intersecting on said portion of said specimen and lying within said opening;

a carriage for supporting said first and second laser sources carriage for movement in two orthogonal directions, said cross hair line formed by said beams being perpendicular and intersecting, said carriage being movable in directions parallel to each of said lines;

the opposite end of the biopsy needle receiving the cross hair line and locating the axis of said needle at an angle with respect to said specimen during insertion and removal of said core sample; and cam means for camming the laser head to a position so that the angle of the cross hair line reduces parallax errors.

* * * * *

UNITED STATES PATENT AND TRADEMARK OFFICE
CERTIFICATE OF CORRECTION

PATENT NO. : 5,320,111
DATED : June 14, 1994
INVENTOR(S) : Livingston

It is certified that error appears in the above-indentified patent and that said Letters Patent is hereby corrected as shown below:

Column 17, line 14, change "abreast" to --a breast--.

Column 17, line 37, change "angles to the vertical as the" to --locations to reduce parallax--.

Column 17, line 57, change "inclination" to --inclinations--.

Column 17, line 57, after "each" insert --of--.

Column 18, line 4, change "type" to --the--.

Signed and Sealed this

Eleventh Day of October, 1994

Attest:

BRUCE LEHMAN

*Attesting Officer*       *Commissioner of Patents and Trademarks*